(12) United States Patent
Tseng et al.

(10) Patent No.: US 11,822,331 B2
(45) Date of Patent: Nov. 21, 2023

(54) THREE-DIMENSIONAL ENVIRONMENTAL COVERAGE ORIENTED MOTION SYSTEM AND METHOD

(71) Applicant: National Central University, Taoyuan (TW)

(72) Inventors: Kuo-Shih Tseng, Taoyuan (TW); Chih-Yuan Chou, Taoyuan (TW)

(73) Assignee: National Central University, Taoyuan (TW)

(*) Notice: Subject to any disclaimer, the term of this patent is extended or adjusted under 35 U.S.C. 154(b) by 769 days.

(21) Appl. No.: 16/993,334

(22) Filed: Aug. 14, 2020

(65) Prior Publication Data
US 2021/0373559 A1    Dec. 2, 2021

(30) Foreign Application Priority Data

Jun. 1, 2020  (TW) .................................. 109118327

(51) Int. Cl.
*G06F 17/00* (2019.01)
*G05D 1/02* (2020.01)
(Continued)

(52) U.S. Cl.
CPC ............ *G05D 1/0212* (2013.01); *A61L 2/025* (2013.01); *A61L 2/07* (2013.01); *A61L 2/10* (2013.01);
(Continued)

(58) Field of Classification Search
CPC ............... G05D 1/0212; G05D 1/0272; G05D 2201/0203; G05D 1/0219; G05D 1/024; G05D 1/0274; A61L 2/025; A61L 2/07; A61L 2/10; A61L 2/20; A61L 2/22; A61L 2/24; A61L 2202/11; A61L 2202/14; A61L 2202/16; A61L 2/18; G01P 3/00;
(Continued)

(56) References Cited

U.S. PATENT DOCUMENTS 7,251,853 B2 * 8/2007 Park ....................... A47L 7/0061
                                              15/340.1
7,836,548 B2 * 11/2010 Cho ........................... A47L 9/04
                                              15/421
(Continued)

FOREIGN PATENT DOCUMENTS

CN       111001025 A    4/2020

OTHER PUBLICATIONS

The use of a UV-C disinfection robot (Year: 2021).*

*Primary Examiner* — Ronnie M Mancho
(74) *Attorney, Agent, or Firm* — Demian K. Jackson; Jackson IPG PLLC (57) ABSTRACT

The present invention relates to an environmental coverage oriented motion system. The system includes a rangefinder module configured to measure a distance in real time; an odometry module configured to measure a velocity or a position in real time; a powered vehicle carrying the rangefinder module and the odometry module; and a controller module carried by the powered vehicle, configured to receive one of the distance, the velocity and the position, performing an environmental coverage oriented motion scheme based on one of the distance, the velocity and the position to select a plurality of positions, and commanding the powered vehicle to move among the plurality of positions.

9 Claims, 8 Drawing Sheets (51) Int. Cl.
*G01S 17/86* (2020.01)
*G01P 3/00* (2006.01)
*A61L 2/24* (2006.01)
*A61L 2/10* (2006.01)
*A61L 2/025* (2006.01)
*A61L 2/22* (2006.01)
*A61L 2/07* (2006.01)
*A61L 2/20* (2006.01)
*G01S 17/88* (2006.01)
*G01S 5/00* (2006.01)
*G01S 5/30* (2006.01)
*G06V 10/10* (2022.01)

(52) U.S. Cl.
CPC .................. *A61L 2/20* (2013.01); *A61L 2/22* (2013.01); *A61L 2/24* (2013.01); *G01P 3/00* (2013.01); *G01S 17/86* (2020.01); *G01S 17/88* (2013.01); *G05D 1/0272* (2013.01); *A61L 2202/11* (2013.01); *A61L 2202/14* (2013.01); *A61L 2202/16* (2013.01); *G01S 5/014* (2020.05); *G01S 5/30* (2013.01); *G05D 2201/0203* (2013.01); *G06V 10/10* (2022.01)

(58) Field of Classification Search
CPC .......... G01S 17/86; G01S 17/88; G01S 5/014; G01S 5/30; G06V 10/10; A47L 2201/04; A47L 2201/06

USPC ....................................................... 700/245
See application file for complete search history.

(56) References Cited

U.S. PATENT DOCUMENTS

| | | | |
|---|---|---|---|
| 7,837,958 B2* | 11/2010 | Crapser | A61L 9/122 422/123 |
| 8,774,970 B2* | 7/2014 | Knopow | A47L 5/28 15/385 |
| 8,779,391 B2* | 7/2014 | Flaherty | A61L 2/10 250/461.1 |
| 9,601,007 B2* | 3/2017 | Ashworth | A61L 2/10 |
| 10,534,367 B2* | 1/2020 | Haegermarck | G05D 1/0274 |
| 10,561,751 B1* | 2/2020 | Yang | H04M 1/17 |
| 10,595,695 B2* | 3/2020 | Landry | A47L 9/2884 |
| 10,758,104 B2* | 9/2020 | Schnittman | A47L 9/106 |
| 10,772,980 B2* | 9/2020 | Stibich | G16H 40/20 |
| 10,877,484 B2* | 12/2020 | Haegermarck | G06T 7/521 |
| 11,169,533 B2* | 11/2021 | Haegermarck | A47L 11/4061 |
| 11,474,533 B2* | 10/2022 | Forsberg | A47L 9/2826 |
| 2016/0221195 A1* | 8/2016 | Ashworth | B25J 5/00 |
| 2021/0373559 A1* | 12/2021 | Tseng | G01S 17/88 |

* cited by examiner

THREE-DIMENSIONAL ENVIRONMENTAL COVERAGE ORIENTED MOTION SYSTEM AND METHOD

FIELD

The present invention relates to a three-dimensional (3D) environmental coverage oriented motion system and method, in particular to a three-dimensional environmental coverage oriented motion system and method suitable for a disinfection robot.

BACKGROUND

In the prior art, there are two existing methods for disinfection robots to plan automatic disinfection scope, and the first method is to remotely operate the robot to move to a fixed point for disinfection, and the first method can be in cooperation with ultraviolet light (UV) disinfection or chemical spray disinfection; the other method is that the robot (such as sweeper robot) performs disinfection during movement along a path. The first method has a disadvantage that the robot can only be remotely controlled to perform disinfection and sterilization task at the fixed point, so the sterilization scope is limited by the straightness of light and there are often sterilization dead ends not be emitted by light. The second method has a disadvantage that the robot can only cover a relatively small scope, and the coverage area can be increased only by more moving paths.

The robots operating the first method are also classified into two types, and the first type of robot is disinfection robot equipment which is manually controlled from a remote end; this type of robot is a popular technology in the prior art, and there are many related patents such as U.S. Pat. No. 9,179,703 B2 "Ultraviolet system for disinfection", in which the disclosed UV disinfection system can be manually operated from a remote end to perform disinfection tasks on specific areas or objects.

The second type of robot is automatic robot disinfection equipment, and the disinfection area of the second type of robot is limited to the path moved. The second type of robot has a built-in intelligent processing unit and environmental sensors that can automatically sense the environment surrounding the robot, and automatically plan the disinfection path and try to find the best moving path and trajectory. This type of robot is also a popular technology in the prior art, and there are related patents such as U.S. Pat. No. 8,779,391 B2 "Sterilization system with ultraviolet emitter for eradicating biological contaminants" and U.S. Pat. No. 7,251,853 B2 "Robot cleaner having floor-disinfecting function".

However, these patents disclosing the second type of robots automatically plan the movement paths based on two-dimensional planar maps, and most of them belong to special applications in two-dimensional space; for example, in U.S. Pat. No. 8,779,391 B2, the UV light emitted by the robot is limited in a specific direction, such as downward direction, and the robot moves on a planar path to cover the area on the path as much as possible. Therefore, the existing technologies and patents have pointed out a problem, that is, how to maximize the coverage scope of automatic disinfection in three-dimensional space has long been a big challenge in the field of computer science.

In fact, to solve the problem of how to maximize the coverage scope of automatic disinfection in three-dimensional space, the first difficulty encountered is the huge amount of computer calculations. In a three-dimensional space to be disinfected, there may be N positions and it is impossible for an automatic disinfection robot to disinfect at all positions, so the robot can only find K specific points, which produce the maximum coverage, from the N positions, and then move to these K specific points to perform disinfection tasks.

However, the amount of calculation required for the above path planning task is (N−K)!, and when N is slightly larger, the robot may not be able to complete the calculation in real time; for example, when N is set to 1000 and 6 specific points are selected (K=6), it takes 0.001 seconds to calculate the coverage once, and it further takes 1000×999×998×997×996×995×0.001=985,084,775,273,880 seconds (about ten billion years) to calculate the 6 specific points which produces maximum coverage scope, and it is impossible for the existing computer science and technology to complete the calculation.

Hence, there is a need to solve the above deficiencies/issues.

SUMMARY

In order to solve the convention problem that the disinfection robot straight moving to the target location is easy to cause a dead end in the disinfection scope, the present invention proposes an environmental coverage oriented motion system for disinfection robots, the system enables the mobile vehicle of the robot to automatically calculate disinfection points which can approximately cover the environment maximally under conditions of known environment map and known environmental coverage function, and move to the disinfection points in sequence to start the disinfection task, thereby achieving the functions of environmental coverage and disinfection.

The present invention provides an innovative and efficient environmental coverage oriented motion calculation method which can calculate coverage of a map covered by light to perform real-time calculation of multiple optimal specific points that can construct approximate maximum coverage. In known two-dimensional environment map or three-dimensional environment map and under the coverage scope of disinfection equipment, the coverages of multiple disinfection points are calculated based on the conditions set by user, for example, the condition can be 10 fixed points or completion within 2 hours; next, some of the disinfection points are selected to perform automatic disinfection, in sequential order.

The present invention provides an environmental coverage oriented motion system, includes a rangefinder module configured to measure a distance in real time; an odometry module configured to measure a velocity or a position in real time; a powered vehicle carrying the rangefinder module and the odometry module; and a controller module carried by the powered vehicle, configured to receive one of the distance, the velocity and the position, performing an environmental coverage oriented motion scheme based on one of the distance, the velocity and the position to select a plurality of positions, and commanding the powered vehicle to move among the plurality of positions.

Preferably, the environmental coverage oriented motion system further includes one of components as follows: a disinfection module configured to electrically connect with the controller module and receive an instruction sent from the controller module to perform a disinfection to a surrounding environment; a communication transmission module being one selected from a wireless radio frequency module, a physical data transmission interface and a data connector, and providing for an external device to perform a data uploading or a data downloading or providing for a user to set up the environmental coverage oriented motion system therethrough, when a connection for data transmission with the external device is established; a memory module configured to electrically connect with the controller module and store an information based on the distance, the velocity or the position, a space coverage function, a space cost function or an environmental map for access; the controller module configured to compute a disinfection coverage for a three-dimensional target space based on the information, and commanding the disinfection module to perform accordingly to fully disinfect a space within the disinfection coverage; and a battery module storing and providing an electrical power required by the rangefinder module, the odometry module, the powered vehicle, the controller module, the disinfection module, the communication transmission module and the memory module to operate.

Preferably, the environmental coverage oriented motion scheme is performed based on one of a space coverage function and a space cost function.

The present invention further provides an environmental coverage oriented motion method including measuring a distance in real time by a rangefinder module in real time; measuring a velocity or a position by an odometry module in real time; receiving one of the distance, the velocity and the position by a controller module; performing an environmental coverage oriented motion scheme based on one of one of the distance, the velocity and the position to select a plurality of positions; and commanding a powered vehicle to move among the plurality of positions by the controller module.

Preferably, the environmental coverage oriented motion method further includes one of steps as follows: performing the environmental coverage oriented motion scheme based on a space coverage function by the controller module; performing a computation to ratio of coverage according to the space coverage function to compute a plurality of surrounding coverage ratios for a plurality of possible positions by the controller module; selecting one having a maximum value among the plurality of surrounding coverage ratios out of the plurality of possible positions every time after the computation is performed and adding it into a goal set in sequence; and determining the plurality of the positions from the plurality of possible positions by the controller module based on the computed plurality of surrounding coverage ratios.

Preferably, the environmental coverage oriented motion method further includes one of steps as follows: performing the environmental coverage oriented motion scheme based on a space cost function by the controller module; performing a computation to ratio of cost coverage according to the space cost function to compute a plurality of surrounding cost coverage ratios for a plurality of possible positions by the controller module; selecting one having a maximum value among the plurality of surrounding cost coverage ratios out of the plurality of possible positions every time after the computation is performed and adding it into a goal set in sequence; and determining the plurality of the positions from the plurality of possible positions by the controller module based on the computed plurality of surrounding cost coverage ratios.

Preferably, the environmental coverage oriented motion method further includes one of steps as follows: establishing one of a space coverage function and a space cost function for a three-dimensional target space; and establishing an environmental map for the three-dimensional target space.

DESCRIPTION OF THE DRAWINGS

A more complete appreciation of the invention and many of the attendant advantages thereof are readily obtained as the same become better understood by reference to the following detailed description when considered in connection with the accompanying drawing, wherein.

DETAILED DESCRIPTION

The present disclosure will be described with respect to particular embodiments and with reference to certain drawings, but the disclosure is not limited thereto but is only limited by the claims. The drawings described are only schematic and are non-limiting. In the drawings, the size of some of the elements may be exaggerated and not drawn on scale for illustrative purposes. The dimensions and the relative dimensions do not necessarily correspond to actual reductions to practice.

It is to be noticed that the term "including", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device including means A and B" should not be limited to devices consisting only of components A and B.

The disclosure will now be described by a detailed description of several embodiments. It is clear that other embodiments can be configured according to the knowledge of persons skilled in the art without departing from the true technical teaching of the present disclosure, the claimed disclosure being limited only by the terms of the appended claims.

Figure 1:
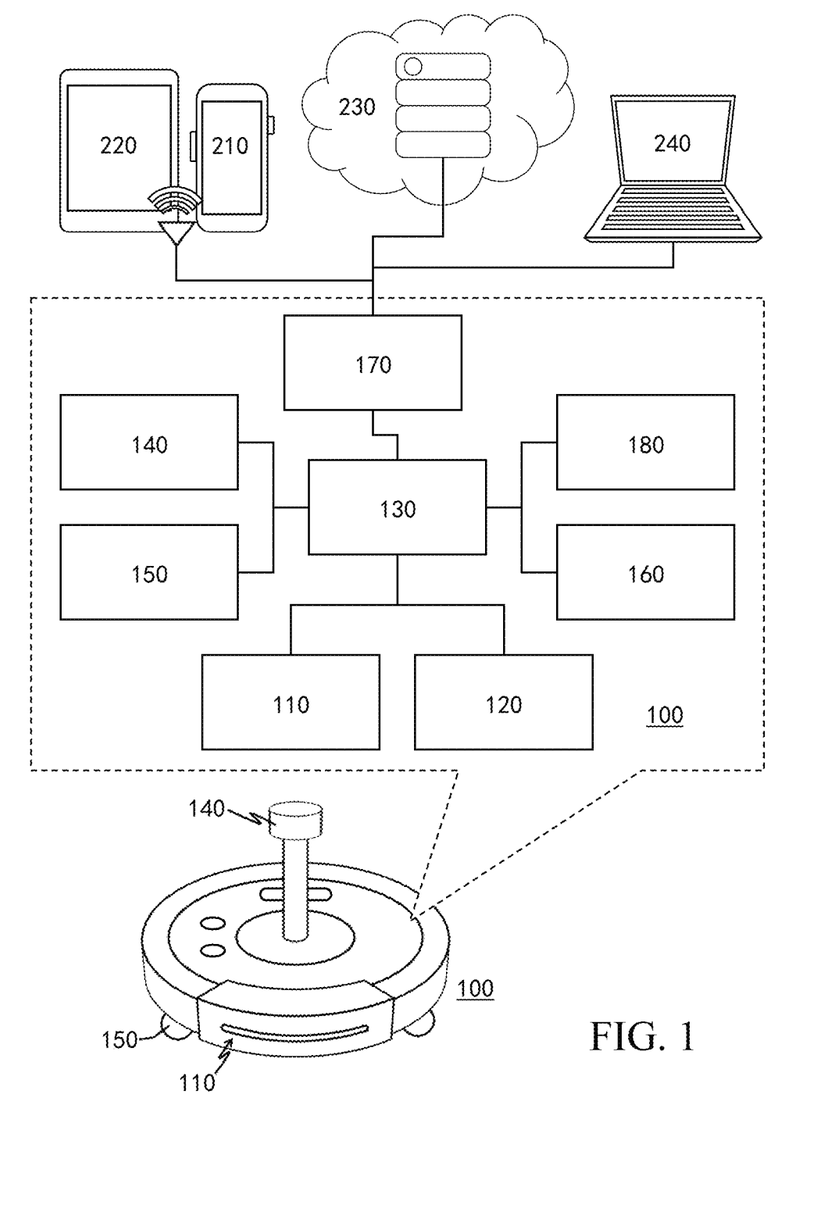
FIG. 1 is a schematic diagram illustrating a system architecture of a three-dimensional environmental coverage oriented motion system in accordance with the present invention.

FIG. 1 is a schematic diagram illustrating a system architecture of a three-dimensional environmental coverage oriented motion system in accordance with the present invention. An environmental coverage oriented motion system 100 of the present invention shown in FIG. 1 includes a rangefinder module 110, an odometry module 120, a controller module 130, a disinfection module 140, a powered vehicle 150, a battery module 160, a communication transmission module 170 and a memory module 180 which are electrically connected to each other. The battery module 160 can provide electrical power required for operations of these modules and vehicles; the controller module 130 modulates and regulates the power provided by the battery module 160, and then provides the power to each of the above-mentioned modules and vehicles. Preferably, the battery module 160 provides DC power with low voltage or low power to the controller module 130.

The disinfection module 140 is a module that can perform disinfection or sterilization on surrounding environment; preferably, the disinfection module 140 can be electromagnetic wave disinfection equipment, ultra-violet disinfection equipment, mechanical wave disinfection equipment, chemical spray disinfection equipment, high temperature liquid sterilization equipment, gas sterilization equipment, high-pressured steam sterilization equipment, high-pressured steam sterilization equipment, or other equipment with the function of disinfection or sterilization. The disinfection module 140 receives a control signal from the controller module 130, and performs disinfection on the surrounding environment. The coverage scope of the disinfection performed by the disinfection module 140 is a three-dimensional space, which belongs to the coverage for three-dimensional space.

The communication transmission module 170 is a communication interface used by the environmental coverage oriented motion system 100 to perform bi-directional data transmission with the external device; preferably, the communication transmission module 170 can be a set of wireless RF modules, a set of physical data transmission interfaces, or a data connector. Through the communication transmission module 170, an external device can upload data, download data, or a user can set the environmental coverage oriented motion system 100 or the controller module 130. The external device can be, for example but not limited to, a smart phone 210, a tablet device 220, a cloud server 230, a notebook computer 240, or a desktop computer.

The rangefinder module 110 can measure a distance of a front object within a sensing scope, and transmit a measurement result to the controller module 130; preferably, the rangefinder module 110 can include at least one distance sensor, and when the rangefinder module includes multiple distance sensors, each sensor can individually sense the distance of the front object, and the system can obtain distance information of large scope by calculating the sensed distances based on the geometric calculation formula. The rangefinder module 110 can be, for example but not limited to, a rangefinder, radar ranging equipment, infrared array ranging equipment, ultrasonic array ranging equipment, an image ranging module or an RGB-D camera ranging module.

The odometry module 120 can be a compound motion sensing module including, preferably, at least one sensor. The at least one sensor can be, for example but not limited to, one of a motion sensor, a motion transducer, a gyroscope, an accelerometer, a tachometer, a movement sensor, an optical encoder, and a combination thereof. The odometry module 120 can measure a forward direction, inertia, movement, position, velocity, acceleration, or time consumption of the powered vehicle 150, and transmit the measured data to the controller module 130. In other embodiment, in the odometry module 120, the movement is estimated by the integral of the measured velocity value over time. The measurement values of the odometry module 120 and the rangefinder module 110 can be referenced and corrected between each other.

Various electronic signals measured by the rangefinder module 110 and the odometry module 120 are transmitted to the controller module 130 for signal processing. The controller module 130 is used as a core operation and control unit of the environmental coverage oriented motion system 100, and can include at least one of a microcontroller (MCU), an electronic control unit (ECU), a central processing unit (CPU), a control circuit unit and a combination thereof. The controller module 130 is preferably designed to use low voltage for low power operation. The controller module 130 receives the measurement signals sensed by the rangefinder module 110 and the odometry module 120, and processes and converts the received signals into actual physical values, such as object distance, heading angle, inertia, movement, coordinates, velocity, acceleration, or time consumption.

The controller module 130 transmits these physical values to an external device through the communication transmission module 170, or stores these physical values in the memory module 180 on the local end for waiting for a user to download. Based on these physical values, the current location of the powered vehicle 150, environment map and disinfection scope can be determined correctly, to find the best movement path. The firmware stored in the controller module 130 is built with an environmental coverage oriented motion method which is implemented on the basis of a space coverage function or a space cost function. After the firmware is executed, the controller module 130 can select disinfection positions and plan a moving path based on the received measurement signals, so as to plan and generate the moving path with maximum space coverage.

The memory module 180 includes read-only memory (ROM) and random-access memory (RAM), and is mainly used to store the above-mentioned physical values, and store the information about the space coverage function, the space cost function, the environment map and other information, which is uploaded from the outside through the communication transmission module 170, for further access.

The powered vehicle 150 is a set of powered mobile platforms for carrying the above-mentioned modules and performing forward, backward, steering and other actions according to control commands. The powered vehicle 150 can be, for example but not limited to, a wheeled vehicle, a tracked vehicle, an omnidirectional wheeled vehicle, an electric vehicle (EV), a car, a motorcycle, a bicycle, a robot platform or other controlled mobile device.

Figure 2:
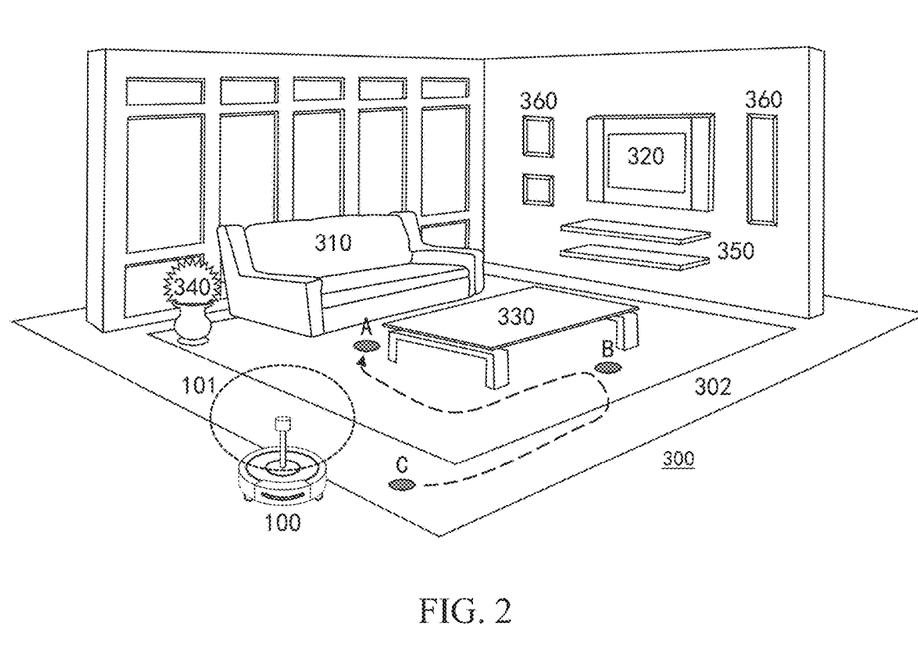
FIG. 2 is a schematic diagram illustrating a target space in which an environmental coverage oriented motion system in accordance with the present invention is set to perform a disinfection task.

FIG. 2 is a schematic diagram illustrating a target space in which an environmental coverage oriented motion system in accordance with the present invention is set to perform a disinfection task. A target space 300 shown in FIG. 2 is a three-dimensional space, many objects are distributed in the target space 300, such as sofa 310, television 320, desk 330, potted plant 340, shelf 350, and calligraphy and painting 360. These objects occupy a part of the target space 300. N positional points on the floor 302 of the target space 300 can be used as disinfection points for the environmental coverage oriented motion system 100, for example, the disinfection positional points include a positional point A, a positional point B, and a positional point C, and so on. The system is to find the position points which is able to produce the maximum disinfection coverage space in the three-dimensional space of the target space 300.

However, no matter what kind of disinfection equipment is installed on the disinfection module 140 of the environmental coverage oriented motion system 100, for example, when the disinfection module 140 is installed with chemical spray disinfection equipment, the three-dimensional conical or spherical spraying scope sprayed to the target space 300 by the disinfection module 140 at different positions are somewhat blocked in different degrees, and it causes dead ends and reduces the disinfection coverage scope; for example, for the three dimensional spherical spraying scope 101 sprayed at the positional point A, most of the spray is obviously blocked by the sofa 310; for the three dimensional spherical spraying scope 101 sprayed at the positional point B, only a small part of the spray is blocked by the desk 330; the three dimensional spherical spraying scope 101 sprayed at the positional point C is almost unblocked and does not produce a disinfection dead end because there is no object near the positional point C, so that a relatively large spatial scope can be covered. Therefore, the disinfection coverage scope of the positional point C, the positional point B and the positional point A are sorted as, in an order from large to small: the positional point C>the positional point B>the positional point A.

When the information of the three-dimensional space to be disinfected is known, the robot can calculate the coverage scope or special coverage of each possible disinfection point, and further derive a space coverage function F. For example, the calculation of coverage can be performed by densely dividing the space within the disinfection scope into three-dimensional virtual grids, and then estimating the coverage scope of disinfection equipment and the number or proportion of virtual grid spaces occupied by the objects in the space, and obtaining the coverage of the single-point disinfection scope of the disinfection point relative to the entire disinfection scope after calculation. When the three-dimensional grids are finer, the coverage of each disinfection point estimated by the robot can be more accurate. In an embodiment, the three-dimensional space grids can be built by uniform grids, non-uniform grids, triangle grids, polygon grids or random grids.

When the coverage of each disinfection point is obtained, the coverage function F can be built; or the coverage can also be obtained by machine learning approaches. Under the condition that the coverage function F is known, it is assumed that there are N disinfection points in the disinfected space, and the N disinfection points form a set s, which includes N disinfection points s={$s_i$, i=1~N} in a disinfected space, and the coverage function of all disinfection points is F($s_i$), i=1~N, wherein i indicates every disinfection point, i=1~N. The coverage function can output the coverage of the set s.

In the first embodiment, N possible disinfection points are selected first in the target space, and the robot is limited to perform fixed-point disinfection at K disinfection points, N is greater than K, and the amount K of the disinfection points can be set by a user. The robot can select K disinfection points from the N possible disinfection points, and then automatically plan the appropriate path, and move to the fixed points for disinfection along the planned path.

At this time, under the limitation that only K disinfection points can be selected, the goal of the robot is to find the K specific points, which can totally produce a larger coverage, from the N possible disinfection point, and the amount of calculation required is (N-K)!; when the values of N is larger, the robot may not complete the calculation in real time. For example, under the condition of N=1000 and K=6, one complete calculation of coverage takes 0.001 seconds, and calculation of the approximate maximum coverage of 6 specific points takes 1000×999×998×997×996×995× 0.001=985,084,775,273,880 seconds (about 100 billion years), and it is impossible for the existing information engineering technology to complete the above-mentioned calculation. Therefore, the present invention proposes an innovation and efficient calculation method to real-time calculate K specific points which can produce a maximum coverage as much as possible.

Figure 3:
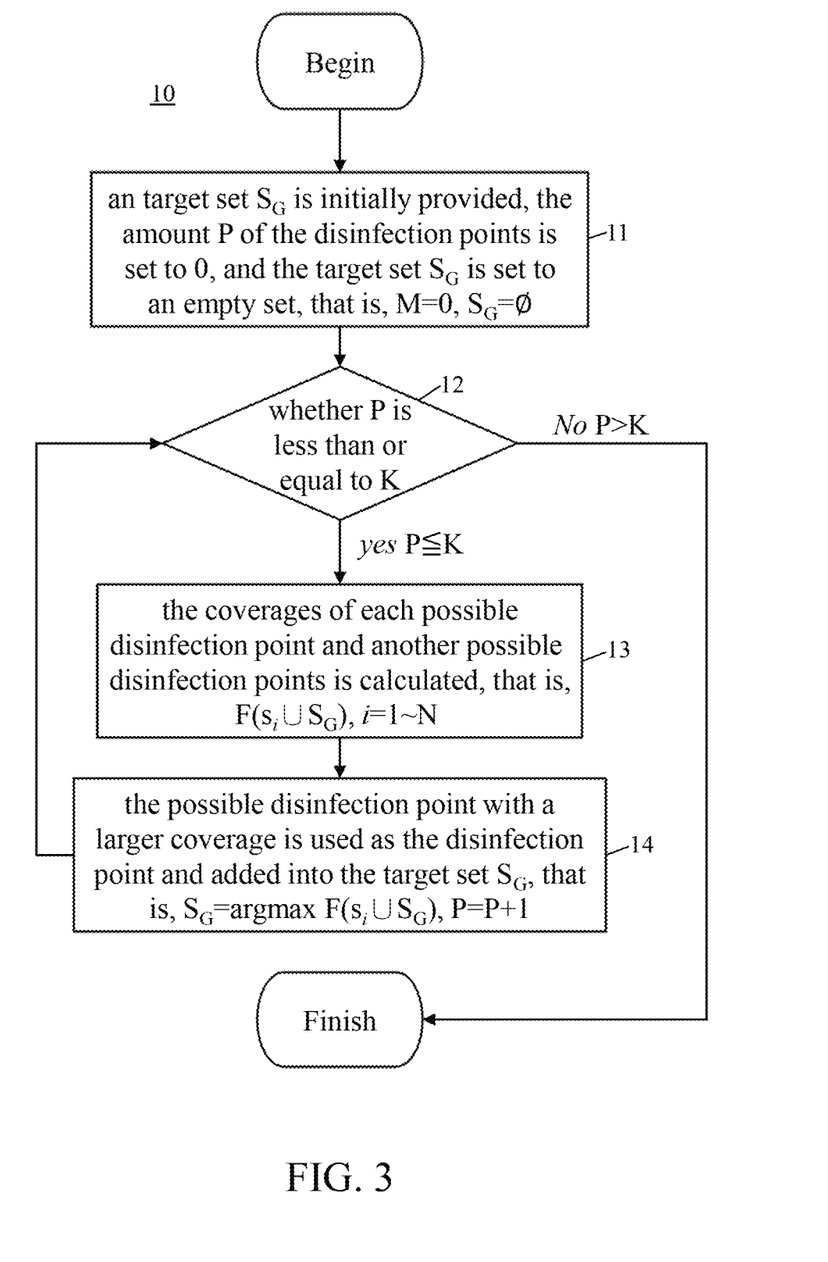
FIG. 3 is a flow chart showing implementation steps of a first embodiment of an environmental coverage oriented motion method in accordance with the present invention.

FIG. 3 is a flow chart showing implementation steps of a first embodiment of an environmental coverage oriented motion method in accordance with the present invention. As shown in FIG. 3, in the first embodiment 10 of the environmental coverage oriented motion method, in a step 11, an target set $S_G$ is initially provided, the amount P of the disinfection points is set to 0, and the target set $S_G$ is set to an empty set, that is, M=0, $S_G$=Ø; in a step 12, it is determined whether P is less than or equal to K; if no, it indicates that P is greater than K and the problem? has been solved, so the method ends; if P is less than or equal to K, in a step 13, the coverages of each possible disinfection point and another possible disinfection points is calculated, that is, F($s_i \cup S_G$), i=1~N; in a step 14, the possible disinfection point with a larger coverage is used as the disinfection point and added into the target set $S_G$, that is, $S_G$=argmax F($s_i \cup S_G$), P=P+1; next, the amount P of the disinfection points is calculated again, and if the amount P of the selected disinfection points is still less than or equal to K, the disinfection point is continuously selected to add into the target set $S_G$, and the step (the step 12) of determining whether the amount P of disinfection points is less than or equal to K is repeated until the amount P of the selected disinfection points is greater than K.

In the second embodiment, the robot finds the disinfection points which produce the largest coverage under the limit condition of cost B. The robot independently calculates the disinfection points to perform disinfection, the cost B can be defined by the user and the cost function C($s_i$) is known; for example, the cost B can be different limit condition such as path length, time or power. The cost condition can be set by the user. When the three-dimensional environmental space information or the two-dimensional environment map information in the scope of disinfection is known, the robot can calculate the cost coverage F($s_i$)/C($s_i$) of each disinfection point based on a space coverage function and a cost function.

Figure 4:
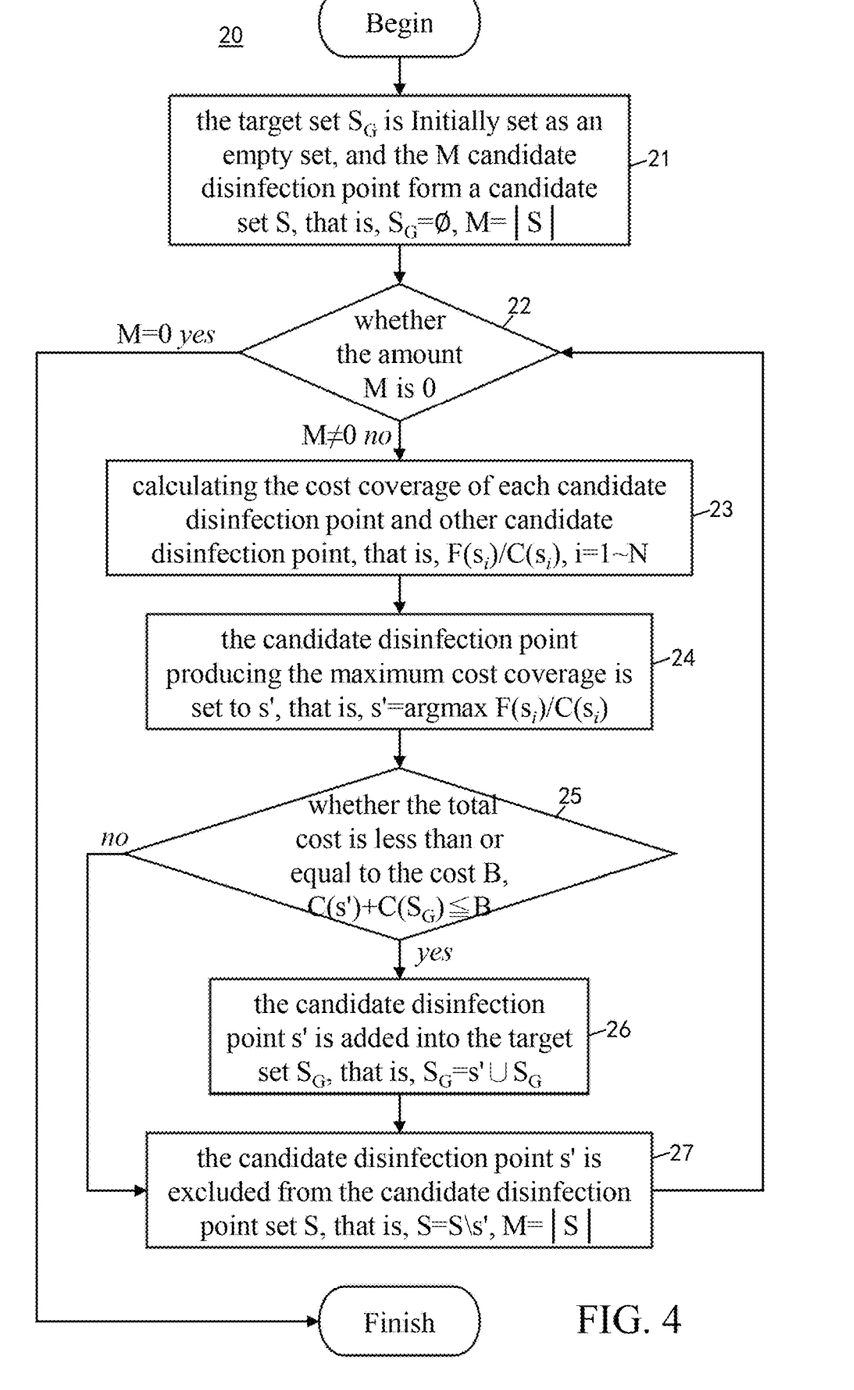
FIG. 4 is a flow chart showing implementation steps of a second embodiment of an environmental coverage oriented motion method in accordance with the present invention.

FIG. 4 is a flow chart showing implementation steps of a second embodiment of an environmental coverage oriented motion method in accordance with the present invention. As shown in FIG. 4, in the second embodiment 20 of the environmental coverage oriented motion method of the invention, in a step 21, the target set $S_G$ is initially set as an empty set, and the M candidate disinfection point form a candidate set S, that is, $S_G$=Ø, M=|S|; in a step 22, it is determined whether the amount M of the candidate disinfection points is 0; If yes, it indicates that there is no candidate disinfection point available for calculation and selection, and the goal of the method is achieved and the calculation method ends; if the amount M of the candidate disinfection points is not 0, in a step 23, calculating the cost coverage of each candidate disinfection point and other candidate disinfection point, that is, F($s_i$)/C($s_i$), i=1~N; in a step 24, the candidate disinfection point producing the maximum cost coverage is set to s', that is, s'=argmax F($s_i$)/C($s_i$).

Next, in a step 25, it is determined whether the total cost is less than or equal to the cost B, that is, C(s')+C($S_G$)≤B; if no, in a step 27, the candidate disinfection point s' is excluded from the candidate disinfection point set S, that is, s=S\s', M=|S|; if the total cost is less than or equal to the cost B, in a step 26, the candidate disinfection point s' is added into the target set $S_G$, that is, $S_{G=}s' \cup S_G$; next, in a step 27, the candidate disinfection point s' is excluded from the candidate disinfection point set S, that is, S=S\s', M=|S|; next, the step (the step 22) of determining whether the amount M of candidate disinfection points is 0 is repeated until the candidate set S becomes an empty set, that is, the amount M of the candidate disinfection points is equal to 0; when the cost of each candidate disinfection point is set to 1, the second embodiment is the same as the first embodiment.

FIG. 5 to FIG. 8 are schematic diagrams illustrating a calculation process of a third embodiment of the environmental coverage oriented motion method in accordance with the present invention. In target space 300 shown in FIG. 5 to FIG. 8, it is assumed that there are five possible disinfection points $s_1 \sim s_5$, that is, N=5; the goal of the third embodiment is to select two disinfection points, that is, K=2. Each possible disinfection point has an environmental coverage thereof, and based on calculation of the coverage function $F(s_i)$, i=1~N, the environmental coverage of the possible disinfection point $s_1$ is $F(s_1)$=0.2, the environmental coverage of the possible disinfection point $s_2$ is $F(s_2)$=0.01, and the environmental coverage of the possible disinfection point $s_3$ is $F(s_3)$=0.002, the environmental coverage of the possible disinfection point $s_4$ is $F(s_4)$=0.005, and the environmental coverage of the possible disinfection point $s_5$ is $F(s_5)$=0.004.

Figure 5:
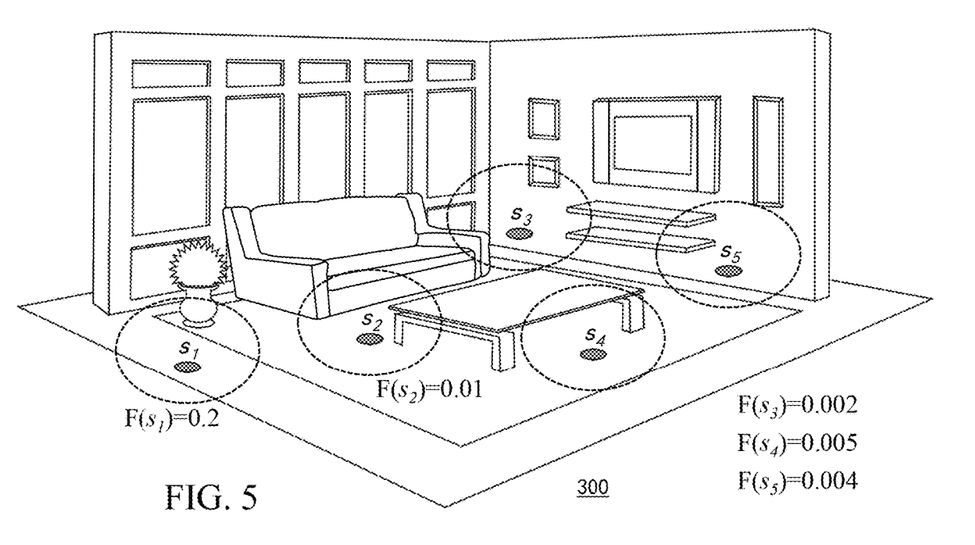
FIG. 5 to FIG. 8 are schematic diagrams illustrating a calculation process of a third embodiment of the environmental coverage oriented motion method in accordance with the present invention.
Figure 6:
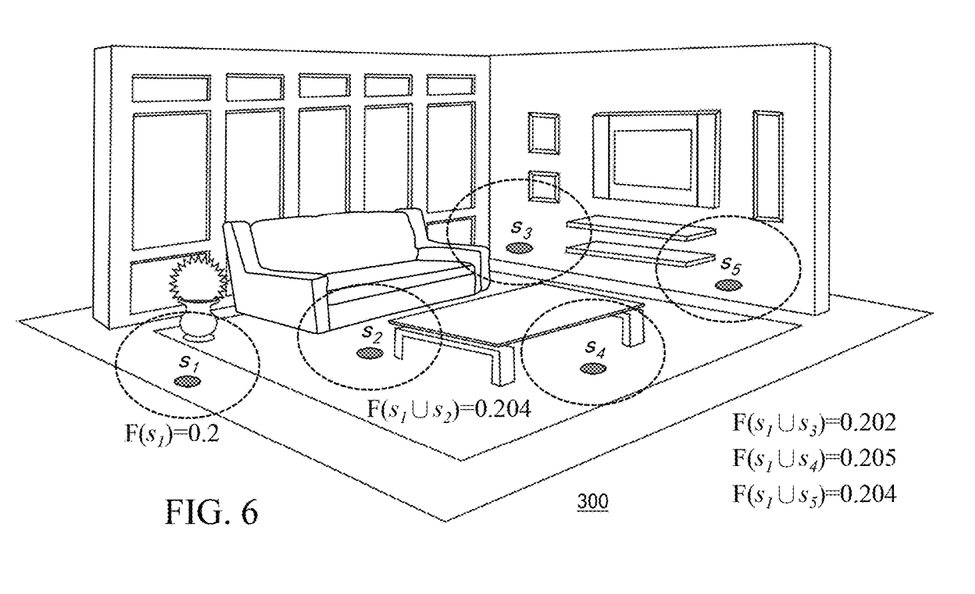
Figure 7:
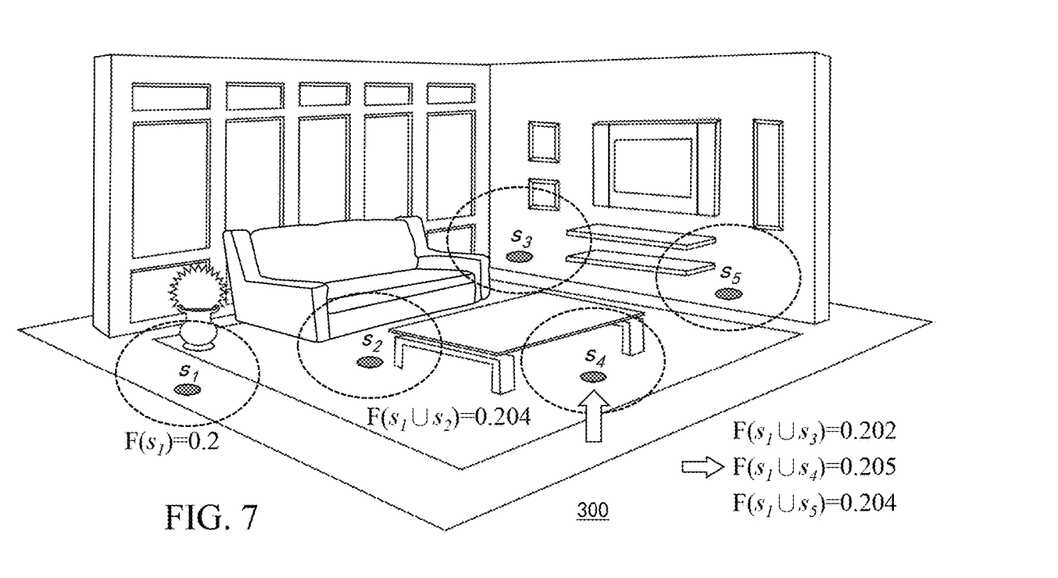
Figure 8:
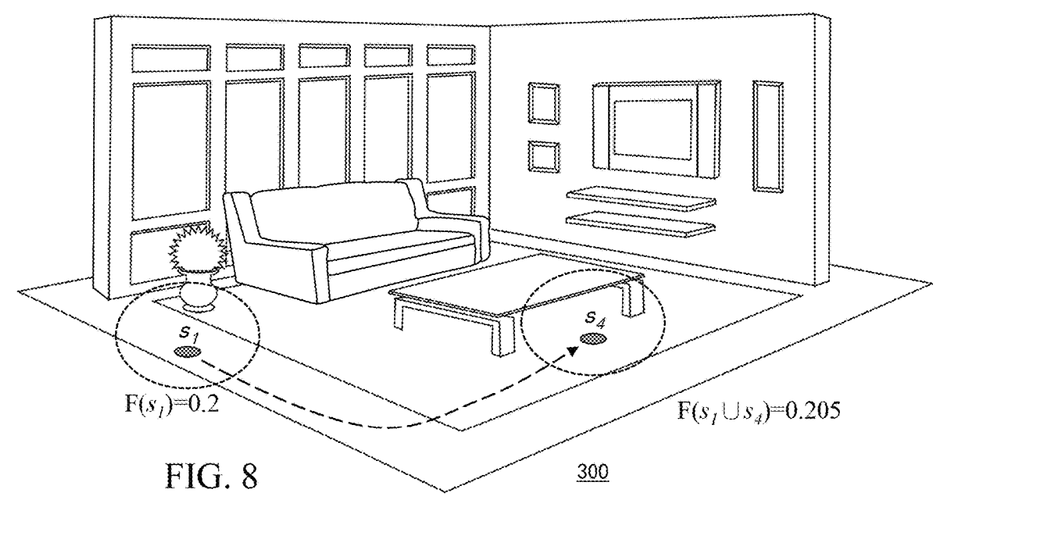

As shown in FIG. 5, the robot calculates the coverage of each disinfection point, and then selects the disinfection point with the largest coverage; in this step, s1 is the disinfection point which produces the largest coverage, as shown in FIG. 6, s1 is selected as the first disinfection point; next, the robot calculates an union of the coverages of another possible disinfection point and the disinfection point s1, and then select the disinfection point which produces the largest union coverage with the disinfection point s1, in this step, the union calculation of the coverage function can obtain: $F(s_1 \cup s_2)$=0.204, $F(s_1 \cup s_3)$=0.202, $F(s_1 \cup s_4)$=0.205, and $F(s_1 \cup s_5)$=0.204, it is obvious that the possible disinfection point $s_4$ is the disinfection point producing the maximum coverage, as shown in FIG. 7, so the robot selects the disinfection point $s_4$ as the second disinfection point. Next, as shown in FIG. 8, the robot sets and plans the movement path based on the two selected disinfection points s1 and s4, and starts moving from the disinfection point s1 to the disinfection point s4.

Figure 9:
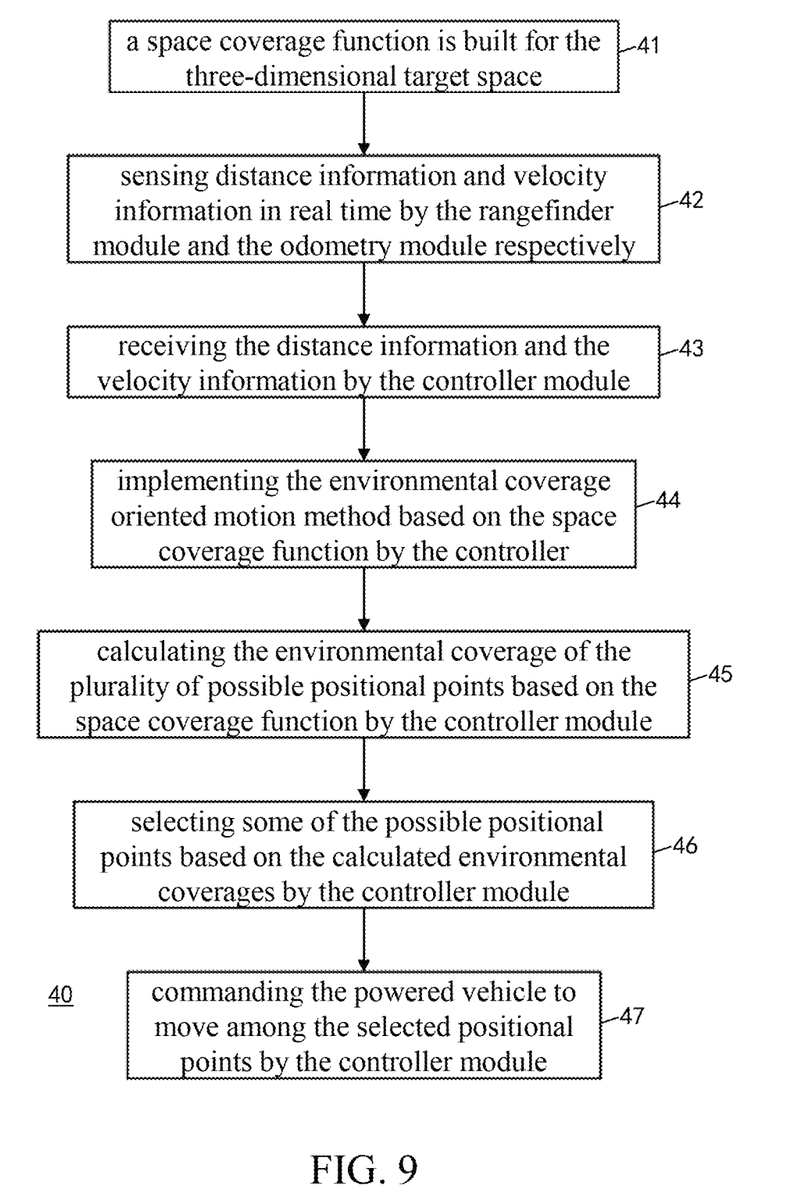
FIG. 9 is a flow chart showing implementation steps of a fourth embodiment of the environmental coverage oriented motion method in accordance with the present invention.

FIG. 9 is a flow chart showing implementation steps of a fourth embodiment of the environmental coverage oriented motion method in accordance with the present invention. In summary, the environmental coverage oriented motion method 40 in accordance with the present invention preferably includes the following steps: in a step 41, a space coverage function is built for the three-dimensional target space; in a step 42, sensing distance information and velocity information in real time by the rangefinder module and the odometry module respectively; in a step 43, receiving the distance information and the velocity information by the controller module; in a step 44, implementing the environmental coverage oriented motion method based on the space coverage function by the controller; in a step 45, calculating the environmental coverage of the plurality of possible positional points based on the space coverage function by the controller module; in a step 46, selecting some of the possible positional points based on the calculated environmental coverages by the controller module; and in a step 47, commanding the powered vehicle to move among the selected positional points by the controller module.

Figure 10:
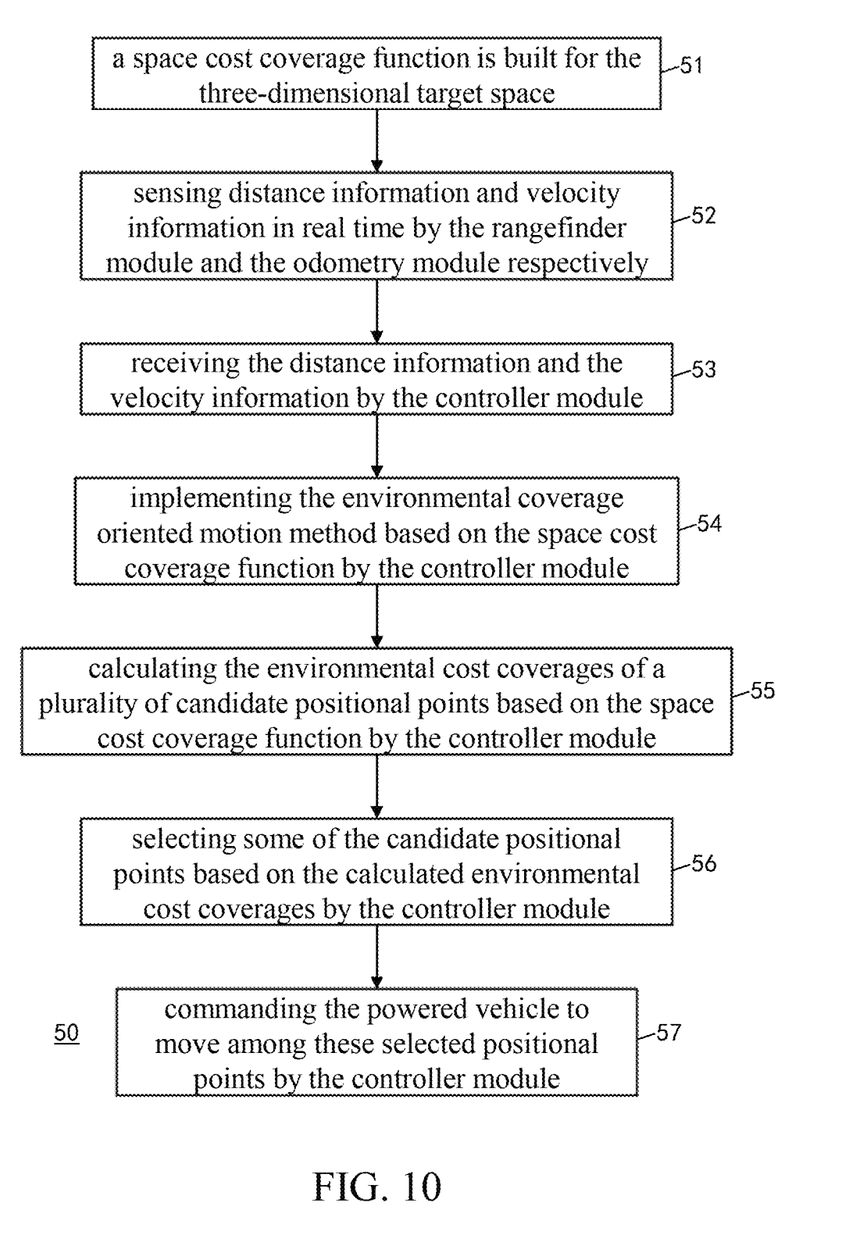
FIG. 10 is a flow chart showing implementation steps of a fifth embodiment of the environmental coverage oriented motion method in accordance with the present invention.

FIG. 10 is a flow chart showing implementation steps of a fifth embodiment of the environmental coverage oriented motion method in accordance with the present invention. In summary, the environmental coverage oriented motion method 50 in accordance with the present invention preferably includes the following steps: in a step 51, a space cost function is built for the three-dimensional target space; in a step 52, sensing distance information and velocity information in real time by the rangefinder module and the odometry module respectively; in a step 53, receiving the distance information and the velocity information by the controller module; in a step 54, implementing the environmental coverage oriented motion method based on the space cost function by the controller module; in a step 55, calculating the environmental cost of a plurality of candidate positional points based on the space cost function by the controller module; in a step 56, selecting some of the candidate positional points based on the calculated environmental cost coverages by the controller module; and in a step 57, commanding the powered vehicle to move among these selected positional points by the controller module.

There are further embodiments provided as follows.

Embodiment 1: An environmental coverage oriented motion system, includes a rangefinder module configured to measure a distance in real time; an odometry module configured to measure a velocity or a position in real time; a powered vehicle carrying the rangefinder module and the odometry module; and a controller module carried by the powered vehicle, configured to receive one of the distance, the velocity and the position, performing an environmental coverage oriented motion scheme based on one of the distance, the velocity and the position to select a plurality of positions, and commanding the powered vehicle to move among the plurality of positions.

Embodiment 2: The environmental coverage oriented motion system as described in Embodiment 1, further inlcues one of components as follows: a disinfection module configured to electrically connect with the controller module and receive an instruction sent from the controller module to perform a disinfection to a surrounding environment; a communication transmission module being one selected from a wireless radio frequency module, a physical data transmission interface and a data connector, and providing for an external device to perform a data uploading or a data downloading or providing for a user to set up the environmental coverage oriented motion system therethrough, when a connection for data transmission with the external device is established; a memory module configured to electrically connect with the controller module and store an information based on the distance, the velocity or the position, a space coverage function, a space cost function or an environmental map for access; the controller module configured to compute a disinfection coverage for a three-dimensional target space based on the information, and commanding the disinfection module to perform accordingly to fully disinfect a space within the disinfection coverage; and a battery module storing and providing an electrical power required by the rangefinder module, the odometry module, the powered vehicle, the controller module, the disinfection module, the communication transmission module and the memory module to operate.

Embodiment 3: The environmental coverage oriented motion system as described in Embodiment 1, the disinfection module includes one selected from a group consisting of an electromagnetic disinfection equipment, an ultraviolet disinfection equipment, a mechanical wave disinfection equipment, a chemical spraying disinfection equipment, a high-temperature fluidic disinfection equipment, a gas-based sterilization equipment, a high-pressure steam disinfection equipment and a combination thereof.

Embodiment 4: The environmental coverage oriented motion system as described in Embodiment 1, the rangefinder module includes one selected from a group consisting of a laser rangefinder, a radar rangefinder, an array-based infrared ray rangefinder, an array-based ultrasonic rangefinder, an image-based rangefinder, a RGB-deep camera rangefinder, and a combination thereof and the odometry module includes one selected from a group consisting of a motion sensor, a motion transducer, a gyroscope sensor, an accelerometer sensor, a tachometer sensor, a displacement sensor, an optical encoder, and a combination thereof.

Embodiment 5: The environmental coverage oriented motion system as described in Embodiment 1, the powered vehicle is a wheel type vehicle, a track type vehicle, an omni-wheel type vehicle, an electric vehicle, a vehicle, a motorcycle, a bicycle, a mobile robot chassis, or a controlled movable device.

Embodiment 6: The environmental coverage oriented motion system as described in Embodiment 1, the environmental coverage oriented motion scheme is performed based on one of a space coverage function and a space cost function.

Embodiment 7: An environmental coverage oriented motion method, includes measuring a distance in real time by a rangefinder module in real time; measuring a velocity or a position by an odometry module in real time; receiving one of the distance, the velocity and the position by a controller module; performing an environmental coverage oriented motion scheme based on one of one of the distance, the velocity and the position to select a plurality of positions; and commanding a powered vehicle to move among the plurality of positions by the controller module.

Embodiment 8: The environmental coverage oriented motion method as described in Embodiment 7, further includes one of steps as follows: performing the environmental coverage oriented motion scheme based on a space coverage function by the controller module; performing a computation to ratio of coverage according to the space coverage function to compute a plurality of surrounding coverage ratios for a plurality of possible positions by the controller module; selecting one having a maximum value among the plurality of surrounding coverage ratios out of the plurality of possible positions every time after the computation is performed and adding it into a goal set in sequence; and determining the plurality of the positions from the plurality of possible positions by the controller module based on the computed plurality of surrounding coverage ratios.

Embodiment 9: The environmental coverage oriented motion method as described in Embodiment 7, further includes one of steps as follows: performing the environmental coverage oriented motion scheme based on a space cost function by the controller module; performing a computation to ratio of cost coverage according to the space cost function to compute a plurality of surrounding cost coverage ratios for a plurality of possible positions by the controller module; selecting one having a maximum value among the plurality of surrounding cost coverage ratios out of the plurality of possible positions every time after the computation is performed and adding it into a goal set in sequence; and determining the plurality of the positions from the plurality of possible positions by the controller module based on the computed plurality of surrounding cost coverage ratios.

Embodiment 10: The environmental coverage oriented motion method as described in Embodiment 7, further includes one of steps as follows: establishing one of a space coverage function and a space cost function for a three-dimensional target space; and establishing an environmental map for the three-dimensional target space.

While the disclosure has been described in terms of what are presently considered to be the most practical and preferred embodiments, it is to be understood that the disclosure need not be limited to the disclosed embodiments. On the contrary, it is intended to cover various modifications and similar arrangements included within the spirit and scope of the appended claims, which are to be accorded with the broadest interpretation so as to encompass all such modifications and similar structures. Therefore, the above description and illustration should not be taken as limiting the scope of the present disclosure which is defined by the appended claims.

What is claimed is:

1. An environmental coverage oriented motion system, comprising:
    a rangefinder module configured to measure a distance in real time;
    an odometry module configured to measure a velocity or a position in real time;
    a powered vehicle carrying the rangefinder module and the odometry module; and
    a controller module carried by the powered vehicle, configured to store a space coverage function which is pre-derived according to a known information of a three-dimensional target space and comprises a relationship of a spatial coverage ratio with respect to each of a plurality of points in the three-dimensional target space, receive one of the distance, the velocity and the position, set a point within the three-dimensional target space as a first disinfection point, compute each of spatial coverage ratios between the first disinfection point and the each of the plurality of points based on the spatial coverage function, select a point having a maximum spatial coverage ratio out of from the plurality of points as a second disinfection point, and command the powered vehicle to move toward the second disinfection point to cover as much three-dimensional space as possible within the three-dimensional target space.

2. The environmental coverage oriented motion system as claimed in claim 1, further comprising one of components as follows:
    a disinfection module configured to electrically connect with the controller module and receive an instruction sent from the controller module to perform a disinfection to a surrounding environment;
    a communication transmission module being one selected from a wireless radio frequency module, a physical data transmission interface and a data connector, and being configured to perform a data uploading or a data downloading when a connection for data transmission with an external device is established;
    a memory module configured to electrically connect with the controller module and store an information based on the distance, the velocity or the position, a space coverage function or an environmental map for access;
    the controller module configured to compute a disinfection coverage for a three-dimensional target space based on the information, and commanding the disinfection module to perform accordingly to fully disinfect a space within the disinfection coverage; and a battery module storing and providing an electrical power required by the rangefinder module, the odometry module, the powered vehicle, the controller module, the disinfection module, the communication transmission module and the memory module to operate.

3. The environmental coverage oriented motion system as claimed in claim 2, wherein the disinfection module comprises one selected from a group consisting of an electromagnetic disinfection equipment, an ultraviolet disinfection equipment, a mechanical wave disinfection equipment, a chemical spraying disinfection equipment, a high-temperature fluidic disinfection equipment, a gas-based sterilization equipment, a high-pressure steam disinfection equipment and a combination thereof.

4. The environmental coverage oriented motion system as claimed in claim 1, wherein the rangefinder module comprises one selected from a group consisting of a laser rangefinder, a radar rangefinder, an array-based infrared ray rangefinder, an array-based ultrasonic rangefinder, an image-based rangefinder, a RGB-deep camera rangefinder, and a combination thereof and the odometry module comprises one selected from a group consisting of a motion sensor, a motion transducer, a gyroscope sensor, an accelerometer sensor, a tachometer sensor, a displacement sensor, an optical encoder, and a combination thereof.

5. The environmental coverage oriented motion system as claimed in claim 1, wherein the powered vehicle is a wheel type vehicle, a track type vehicle, an omni-wheel type vehicle, an electric vehicle, a vehicle, a motorcycle, a bicycle, a mobile robot chassis, or a controlled movable device.

6. The environmental coverage oriented motion system as claimed in claim 1, wherein the environmental coverage oriented motion scheme is performed based on a space coverage function.

7. An environmental coverage oriented motion method, comprising:

establishing a space coverage function which is pre-derived according to a known information of a three-dimensional target space and comprises a relationship of a spatial coverage ratio with respect to each of a plurality of points in the three-dimensional target space;

measuring a distance in real time by a rangefinder module in real time;

measuring a velocity or a position by an odometry module in real time;

receiving one of the distance, the velocity and the position by a controller module;

setting a point within the three-dimensional target space as a first disinfection point, computing each of spatial coverage ratios between the first disinfection point and the each of the plurality of points based on the spatial coverage function, selecting a point having a maximum spatial coverage ratio out of from the plurality of points as a second disinfection point; and commanding a powered vehicle to move toward the second disinfection point by the controller module to cover as much three-dimensional space as possible within the three-dimensional target space.

8. The environmental coverage oriented motion method as claimed in claim 7, further comprising one of steps as follows:

performing the environmental coverage oriented motion scheme based on the space coverage function by the controller module;

performing a computation to ratio of coverage according to the space coverage function to compute a plurality of surrounding coverage ratios for a plurality of possible positions by the controller module;

selecting one having a maximum value among the plurality of surrounding coverage ratios out of the plurality of possible positions every time after the computation is performed and adding it into a goal set in sequence; and determining the plurality of the positions from the plurality of possible positions by the controller module based on the computed plurality of surrounding coverage ratios.

9. The environmental coverage oriented motion method as claimed in claim 7, further comprising one of steps as follows:

establishing one of a space coverage function for a three-dimensional target space; and establishing an environmental map for the three-dimensional target space.

* * * * *